US010660644B2

(12) United States Patent
Robbins et al.

(10) Patent No.: US 10,660,644 B2
(45) Date of Patent: May 26, 2020

(54) RECTAL BAND LIGATION DEVICE AND METHOD OF OPERATION THEREOF

(71) Applicant: Logan Medical Devices, Inc., Dallas, TX (US)

(72) Inventors: Dennis I. Robbins, Dallas, TX (US); David H. Hitt, Dallas, TX (US)

(73) Assignee: Logan Medical Devices, Inc., Dallas, TX (US)

( * ) Notice: Subject to any disclaimer, the term of this patent is extended or adjusted under 35 U.S.C. 154(b) by 251 days.

(21) Appl. No.: 15/782,377

(22) Filed: Oct. 12, 2017

(65) Prior Publication Data

US 2018/0317923 A1    Nov. 8, 2018

Related U.S. Application Data

(60) Provisional application No. 62/408,302, filed on Oct. 14, 2016.

(51) Int. Cl.
*A61B 17/12* (2006.01)
*A61B 17/00* (2006.01)
*A61B 90/00* (2016.01)
*A61B 17/30* (2006.01)

(52) U.S. Cl.
CPC .. *A61B 17/12009* (2013.01); *A61B 17/12013* (2013.01); *A61B 2017/00566* (2013.01); *A61B 2017/00778* (2013.01); *A61B 2017/00818* (2013.01); *A61B 2017/00907* (2013.01); *A61B 2017/12018* (2013.01); *A61B 2017/306* (2013.01); *A61B 2090/0807* (2016.02)

(58) Field of Classification Search
CPC .............. A61B 17/12; A61B 17/12009; A61B 17/12013; A61B 2017/00818; A61B 2017/12018
See application file for complete search history.

(56) References Cited

U.S. PATENT DOCUMENTS

| 5,507,797 | A | * | 4/1996 | Suzuki ............. A61B 17/12013 606/139 |
| 5,741,273 | A |   | 4/1998 | O'Regan |
| 6,818,432 | B2 |  | 11/2004 | Farwick et al. |
| 7,205,131 | B2 |  | 4/2007 | Farwick et al. |

(Continued)

FOREIGN PATENT DOCUMENTS

| WO | 2013-130658 A1 | 9/2013 |
| WO | 2015-026377 A1 | 2/2015 |

(Continued)

*Primary Examiner* — Ashley L Fishback

(57) ABSTRACT

A rectal band ligation device and a method of operating the band ligation device. In one embodiment, the band ligation device includes: (1) a handle having a trigger associated therewith, (2) an extension tube extending from the handle and terminating in a head, (3) at least two openings in the head, (4) hollow pistons located in the openings and configured to move relative thereto between an extended position in which ends of the pistons are exposed through the openings and a retracted position, gaps between corresponding openings and hollow pistons being less than cross-sectional widths of elastic members stretched around the ends and (5) an actuating rod coupling the trigger and the pistons and configured to cause the pistons to move from the extended position to the retracted position.

11 Claims, 4 Drawing Sheets

(56) References Cited

U.S. PATENT DOCUMENTS

| | | | |
|---|---|---|---|
| 8,057,386 B2 * | 11/2011 | Aznoian | A61B 1/00087 |
| | | | 600/104 |
| 9,101,360 B2 | 8/2015 | Chotenovsky et al. | |
| 9,622,750 B2 | 4/2017 | Chotenovsky et al. | |
| 9,693,778 B2 | 7/2017 | Kamler | |
| 2010/0063517 A1 | 3/2010 | Cleator | |
| 2013/0226198 A1 | 8/2013 | Kamler | |
| 2015/0057678 A1 | 2/2015 | Chotenovsky et al. | |
| 2015/0057679 A1 | 2/2015 | Chotenovsky et al. | |
| 2015/0057680 A1 | 2/2015 | Chotenovsky et al. | |
| 2016/0157866 A1 | 6/2016 | Chotenovsky et al. | |
| 2016/0220258 A1 * | 8/2016 | Xu | A61B 17/12013 |

FOREIGN PATENT DOCUMENTS

| | | |
|---|---|---|
| WO | 2015-026378 A1 | 2/2015 |
| WO | 2015-026379 A1 | 2/2015 |
| WO | 2017-106933 A1 | 6/2017 |

* cited by examiner

RECTAL BAND LIGATION DEVICE AND METHOD OF OPERATION THEREOF

CROSS-REFERENCE TO RELATED APPLICATIONS

This application claims priority based on U.S. Provisional Patent Application Ser. No. 62/408,302 filed on Oct. 14, 2016, by Markle, et al., and entitled "Rectal injection Device and Methods of Manufacture and Operation Thereof," commonly owned with this application and incorporated herein by reference.

TECHNICAL FIELD

This application is directed, in general, to a band ligation device and, more specifically, to a rectal band ligation device for hemorrhoids and methods of manufacturing and operating the same.

BACKGROUND

Every year hundreds of millions of individuals worldwide suffer from serious lower gastrointestinal (GI) diseases and disorders (e.g., fecal anal incontinence/laxity, hemorrhoids, colitis) requiring intervention. The technology incorporated in the design of gastrointestinal devices has seen little to no developmental progress in recent years. Indeed, biopsy forceps, polypectomy snares and fine aspiration needles have seen so little change that they are becoming commodities. Though these conventional devices remain limited in their efficacy, the incidence of these disease states continues to increase.

Many other GI disorders have a major impact on health. For example, hemorrhoids—inflamed and swollen veins in the anus or lower rectum—are extremely common, accounting for some 50 million procedures performed worldwide. The two most common office-based procedures used to treat symptomatic hemorrhoids are rubber band ligation (RBL) and sclerotherapy (SCL). RBL involves stretching an elastomeric band (that need not be rubber) about a target vein so that it constricts and substantially halts blood flow through the vein, causing it to shrivel over time, thus reducing and eliminating the hemorrhoid.

SUMMARY

One aspect provides a rectal band ligation device. In one embodiment, the band ligation device includes: (1) a handle having a trigger associated therewith, (2) an extension tube extending from the handle and terminating in a head, (3) at least two openings in the head, (4) hollow pistons located in the openings and configured to move relative thereto between an extended position in which ends of the pistons are exposed through the openings and a retracted position, gaps between corresponding openings and hollow pistons being less than cross-sectional widths of elastic members stretched around the ends and (5) an actuating rod coupling the trigger and the pistons and configured to cause the pistons to move from the extended position to the retracted position.

In another embodiment, the band ligation device includes: (1) a handle having a trigger associated therewith, (2) an extension tube extending from the handle and terminating in a head, the head being of larger diameter than the extension tube and configured to seat on an anal dentate of a rectum, (3) at least two openings in the head, (4) hollow pistons located in the openings and configured to move relative thereto between an extended position which ends of the pistons are exposed through openings and a retracted position, gaps between corresponding openings and hollow pistons being less than cross-sectional widths of elastic members stretched around the ends and (5) an actuating rod coupling the trigger and the pistons and configured to cause the pistons to move from the extended position to the retracted position.

Another aspect provides a method of operating a rectal band ligation device. In one embodiment, the rectal band ligation device includes: (1) inserting a head of the device into a rectum of an animal, (2) creating a suction within the head to cause tissue in the rectum to enter the head through multiple openings thereof and (3) releasing elastic bands surrounding at least some of the openings onto the tissue, causing the elastic bands to bear upon and constrict blood flow to the tissue.

BRIEF DESCRIPTION

Reference is now made to the following descriptions taken in conjunction with the accompanying drawings, in which.

DETAILED DESCRIPTION

Figure 1:
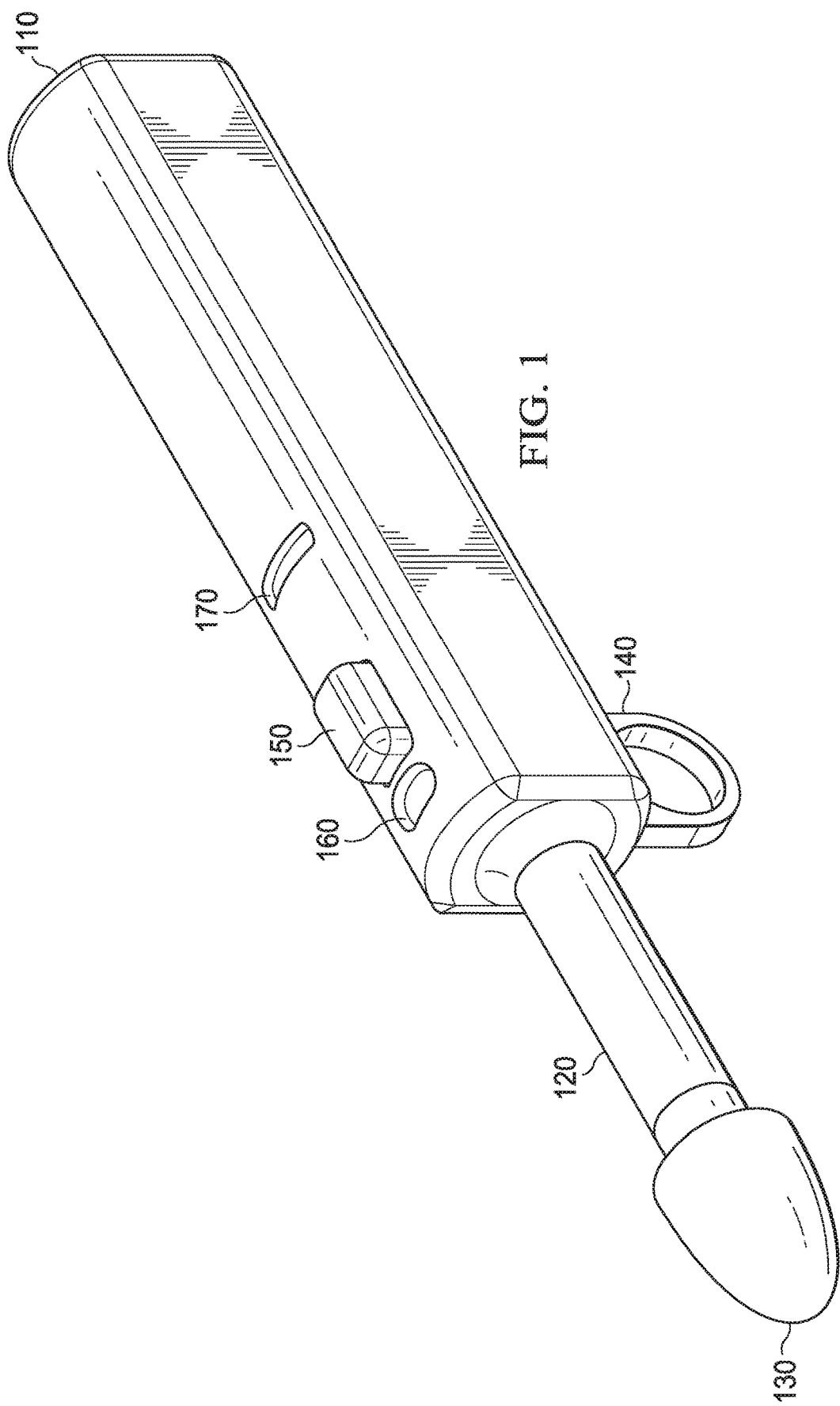
FIG. 1 is an isometric view of one embodiment of a rectal band ligation device.

Introduced herein are various embodiments of a device and method for performing RBL to address hemorrhoids or other concerns. A device providing for RBL for the treatment of hemorrhoidal tissue is also described herein. The device is capable of treating multiple separate sites concurrently and without need for visualization. In other words, the clinician does not need to see the target area to operate on it.

The band ligation device and method may be used in a form integrated with the injection array device described in patent application Ser. No. 15/625,552 filed on Jun. 16, 2017, by Markle, et al., and entitled "Rectal Injection Device and Method of Operation Thereof," commonly owned with this application and incorporated herein by reference. In the case where an integrated version of the device is used, the advantage to the practitioner and the patient is the ability to provide both RBL and sclerotherapy (SOL) to the hemorrhoidal tissue in a single procedure, minimizing discomfort and the need for repeated procedures and appointments. The use of the integrated version may be most suitable to more severe cases of hemorrhoids, where neither banding nor SCL alone provide adequate treatment of the condition.

Many of the various band ligation device embodiments are used as follows: (1) a head of the device is inserted into the rectum of a subject animal or human past the anal dentate line; (2) suction is created within the head to cause tissue in the rectum to enter the head through multiple openings thereof; (4) elastic bands surrounding at least some of the openings are released onto the tissue, causing them to bear upon and constrict blood flow to the tissue; and (5) the device is withdrawn. Constriction of the blood flow effects the treatment, whether it be for hemorrhoids or another condition. In certain embodiments, the head is or becomes enlarged in terms of its diameter such that it seats against the internal sphincter. This allows a clinician operating the device some assurance that the head is properly located within the patient without needing to see the head, e.g., using a scope). Of course, a scope may be employed.

In certain embodiments, the head is bulbous. In other embodiments, the head is conical or frustoconical.

In certain other embodiments, the multiple openings are evenly spaced circumferentially about the head, to cause the elastic bands to treat evenly spaced regions of the rectum with a single pass. In other embodiments, the openings are irregularly spaced.

In some embodiments, the openings lie in single plane normal to a major axis of the device. In other embodiments, the openings are not confined to a single plane and may be distributed about the head in various locations.

In one embodiment, the head has only two openings. Other embodiments contain more, and perhaps many more, openings.

In certain embodiments, hollow pistons extend into the openings and are employed to hold the elastic bands. After suction urges tissue to enter the openings and the hollow pistons, the pistons may then be retracted, which urges the elastic bands off the pistons and onto the tissue, thereby carrying out RBL. In one embodiment, an actuating rod may rotate or translate to cause the pistons to retract and the elastic bands to be deployed. In other embodiments, the needles rotate to deploy and retract. In some embodiments, the pistons are spring-loaded so that they retract in the absence of another force.

In many embodiments, the actuating rod is common to all pistons in a given device. In other embodiments, multiple actuating rods or actuators may allow elastic bands to be deployed individually or in subsets.

In another embodiment, an optical endoscopic functionaity may be integrated with the ligation device to aid in the accurate location RBL sites, and to provide visualization of the RBL site during deployment of elastic bands. A sufficiently low-cost camera may be used in this integration to enable the cost-effective one-time-use of the device.

In another embodiment, the device may be used for the purpose of providing for SCL for esophageal varices.

FIG. 1 is an isometric view of a linear embodiment of a rectal band ligation device 100. The device 100 has an elongated handle 110, an extension tube 120 extending from the handle 110 and a head 130. The handle 110 is configured to be gripped by a human hand. The head 130 is configured to be inserted into a rectum of an animal, which may be a human, treat the rectum with RBL via a plurality of elastic bands (not shown in FIG. 1) and be withdrawn from the rectum.

In the illustrated embodiment, the head 130 is bulbous. The extension tube 120 supports the head relative to the handle 110. A trigger 140 extends laterally from the handle and is configured to be moved to cause tissue (which may be hemorrhoidal or proximate hemorrhoidal tissue) to be drawn into openings (not shown) in the head 130 and banded. In the illustrated embodiment, the trigger 140 is located beneath the handle 110 and configured to be translated away from the head 130 to cause a suction to be drawn through the openings and thereby cause tissue to be drawn into the openings. An RBL button 150 also extends laterally from the handle and is configured to be depressed to perform RBL with respect to the tissue. In the illustrated embodiment, the RBL button 150 is opposite the handle 110 from the trigger 140, and therefore over the handle 110, as shown.

Two indicators are shown in the handle 110. From left to right, they are: a suction indicator 160 configured to indicate whether or not a suction sufficient for RBL has been drawn and an elastic band deployment indicator 170 configured to indicate whether or not RBL has been performed.

Figure 2:
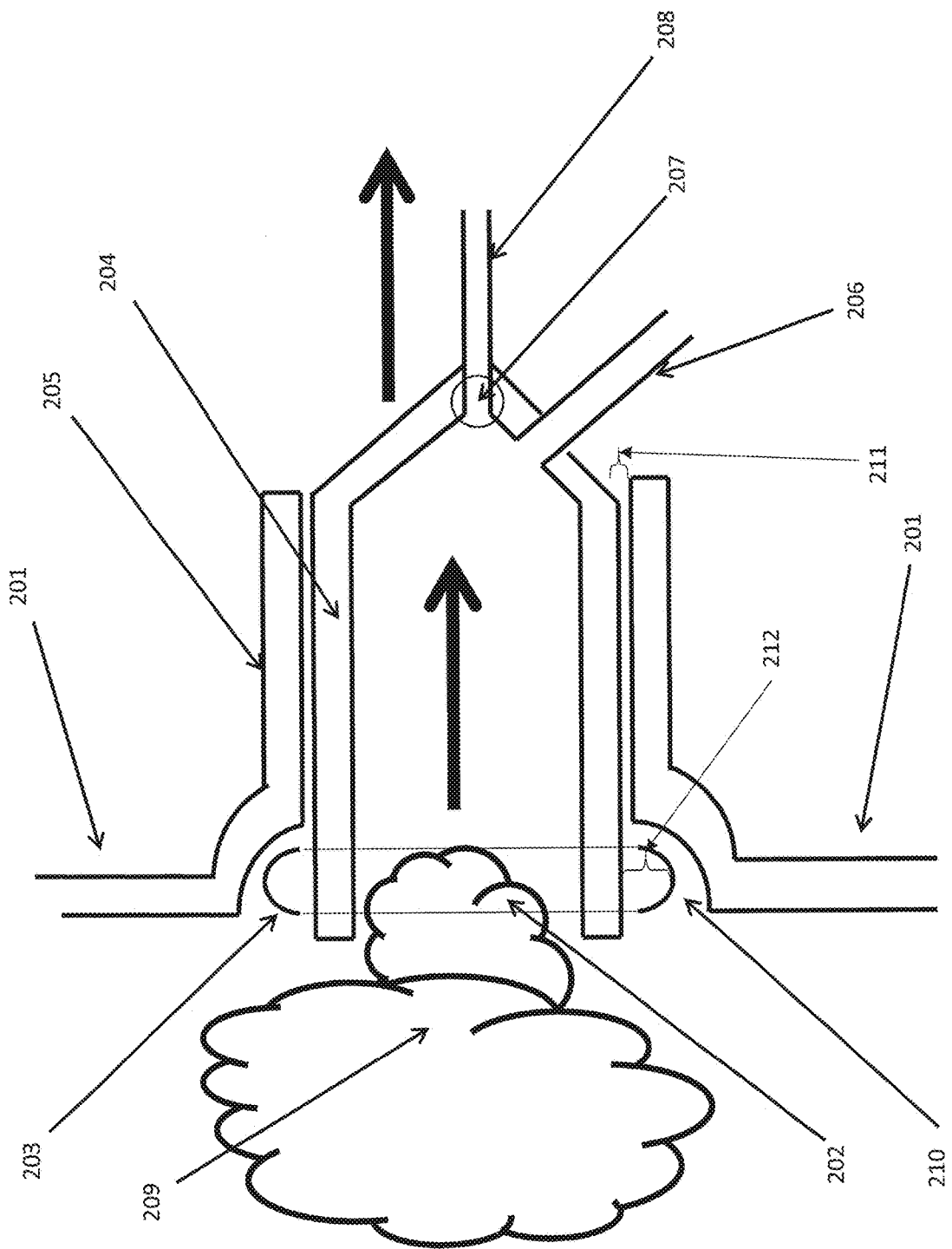
FIG. 2 is a partial lateral sectional view of the rectal band ligation device of FIG. 1.
Figure 3:
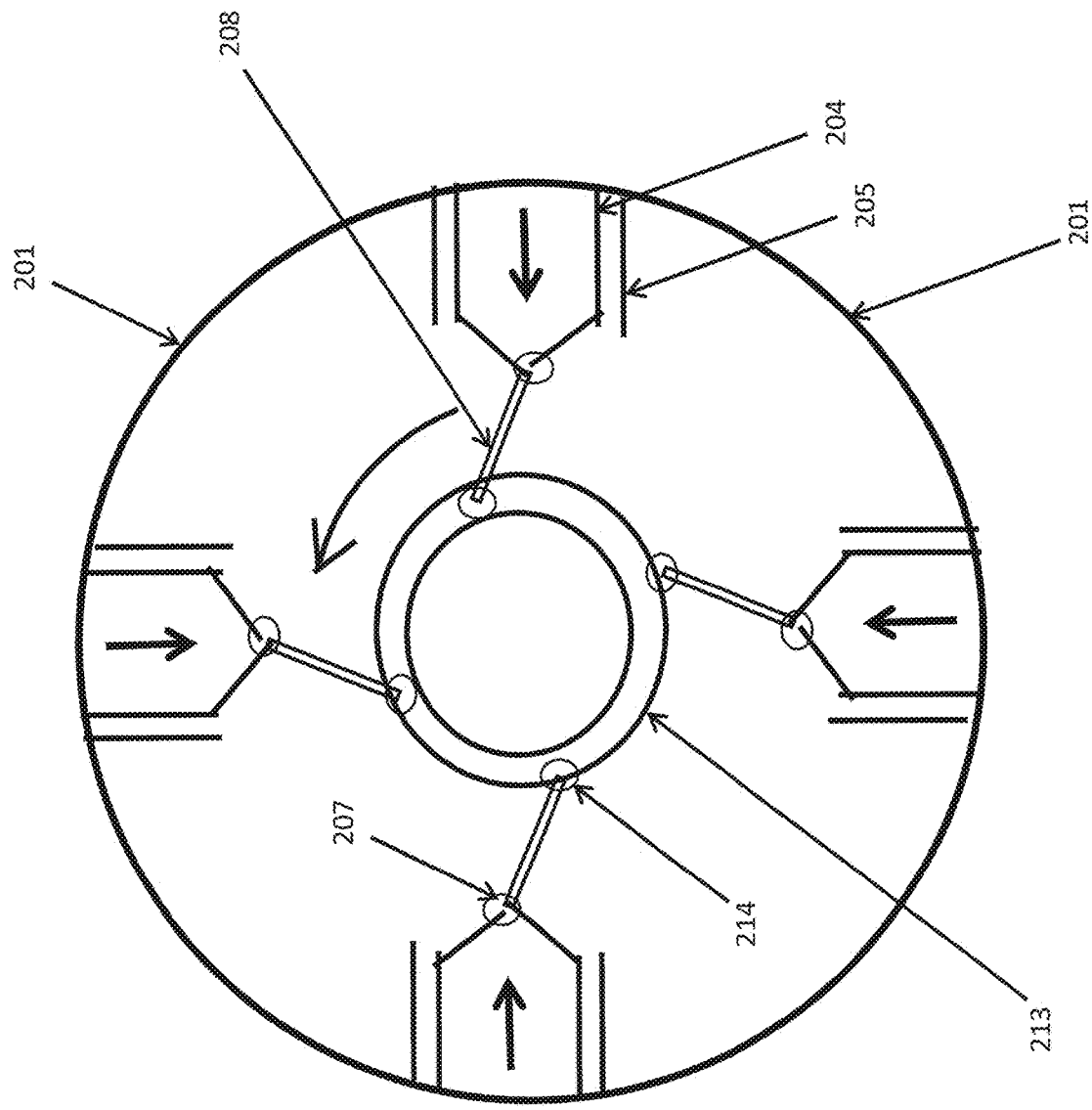
FIG. 3 is an axial sectional view of the rectal band ligation device of FIG. 2.

As illustrated in FIGS. 2 and 3, the band ligation device includes a head 201 which is at least somewhat hollow, and multiple openings 202 in the head 201, in which tissue 209 may be drawn into such openings 202 via suction, e.g., drawn through a suction port 206, for the purpose of performing RBL of the tissue 209. Elastic bands 203 are positioned around the circumference of the openings 202 by means of being placed on a hollow piston 204 before using the device 100. The piston 204 moves inside a sleeve 205, and is drawn inward after the tissue 209 has been drawn into the opening 202 via suction, causing the elastic band 203 to release and engage the tissue 209. The suction may be provided by a plunger (not shown) that may be withdrawn to create a partial vacuum, by means of a vacuum hose or line (not shown) powered externally providing a partial vacuum or by other means in which a partial vacuum may be created. Those ordinarily skilled in the pertinent art will understand various ways to create a suction in the device 100 of FIG. 1.

As is apparent in FIG. 2, a gap 211 exists between an inner surface of the sleeve 205 (which defines the opening) and an outer surface of the piston 204. This gap 211 is less than a cross-sectional width 212 of the elastic band 203. This is to force the elastic band 203 off the end of the piston 204 and onto the tissue 209 as the piston 204 retracts, rater than allow the elastic band 203 to enter the gap and retract with the piston 204.

In the embodiment of the FBI, or combination device illustrated in FIGS. 2 and 3, to release the elastic bands 203 positioned around the pistons 204, the pistons 204 are drawn radially inwards towards the axis of the head. 201 by mechanical, hydraulic, or electrical means, causing the elastic bands 203 to be released onto the tissue 209 as they are pulled against the exterior of the head 201. The head 201 may include recesses 210 to allow for placement of the elastic bands 203 on the outside of the piston 204. In one embodiment, the pistons 204 may be actuated to draw inwards by means of a cam mechanism or linkage (comprising connecting rods 208 flexibly coupled to the pistons 204 and a rotatable actuating rod 213 positioned at or proximate the axis of the head 201 by respective hinges 207, 214. In the case of the band ligation device integrated with an injection device, the cam mechanism or linkage may be situated on a sleeve (not shown) containing an actuation mechanism for the injector needles and tubes transporting the sclerosing agent. Rotation of the actuating rod 213 may be actuated by the practitioner from the handle of the device and may be coupled to a trigger (e.g., the trigger 140 of FIG. 1) or other mechanism to provide for rotation. In an alternative embodiment, the actuating rod 213 may be translated along the axis of the head 201 similarly to draw the pistons 204 radially inwardly.

The head of the RBL or combination device is inserted into the rectum of the patient and is positioned in a manner such that the opening(s) 202 in the head 201 are proximate to the tissue 209 which is to be drawn into the openings 202 and into the pistons 204 for banding.

The RBL or combination SCL/RBL device may be used as a disposable form, or may be fabricated from materials suitable sterilization, and be reused following cleaning and sterilization.

The RBL or combination SCL/RBL device may be fabricated from transparent materials, e.g., transparent plastic such as polycarbonate, allowing for the placement of a suitable camera, or cameras, with illumination, in the interior of the device, to enable viewing and positioning of the device by the practitioner during its use. In the case where one or more cameras are positioned inside the device, having suitable transparency, the source of illumination may be positioned at an oblique angle to the surface of the transparent walls of the device relative to the camera position, to minimize specular reflection. Components in the interior of the device may be provided with a matte black finish to minimize unwanted reflections of the illumination. When used with such camera or cameras, the device may comprise an injection array device, a band ligation device, or a combination device with both functionalities.

The RBL or combination SOL/RBL device may be used in a "blind" mode, in which the location of the tissue is determined in advance by the practitioner, and the device is positioned in the approximate location required for banding of such tissue, or it may be used in guided mode with vision provided by camera(s) as described above. Typically between one and six bands may actually be applied during used of the device.

Figure 4:
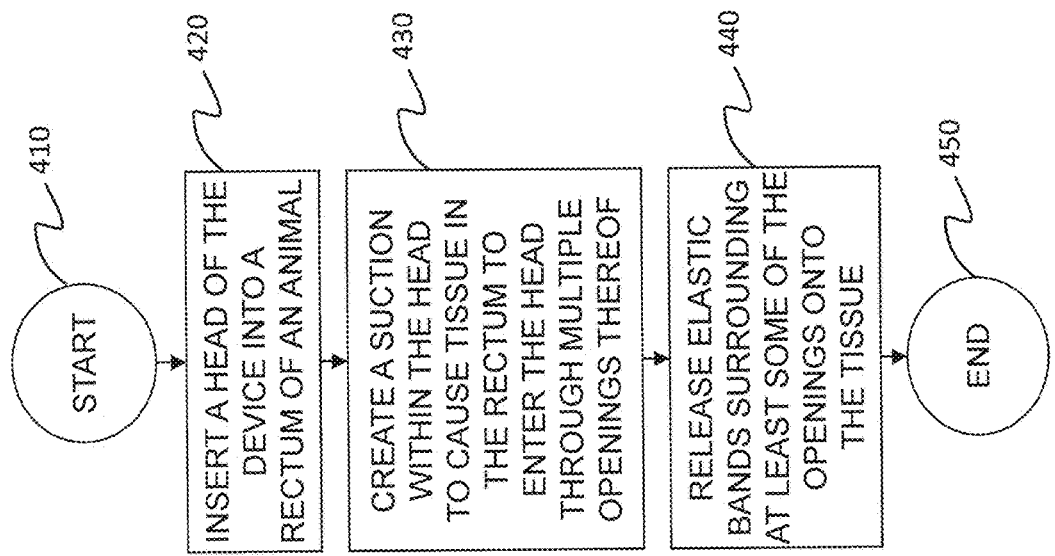
FIG. 4 is a flow diagram of one embodiment of a method of using a rectal band ligation device.

FIG. 4 is a flow diagram of one embodiment of using a rectal band ligation device. The method begins in a start step 410. In a step 420, a head of the device is inserted into a rectum of an animal. In a step 430, a suction is created within the head to cause tissue in the rectum to enter the head through multiple openings thereof. In a step 440, elastic bands surrounding at least some of the openings onto the tissue are released. This causes the elastic hands to bear upon and constrict blood flow to the tissue. The device may then be withdrawn from the rectum. The method ends in an end step 450.

Those skilled in the art to which this application relates will appreciate that other and further additions, deletions, substitutions and modifications may be made to the described embodiments.

What is claimed is:

1. A rectal band ligation device, comprising:
 a handle having a trigger associated therewith;
 an extension tube extending from said handle and terminating in a head;
 at least two openings in said head;
 hollow pistons located in said openings and configured to move relative thereto between an extended position in which ends of said pistons are exposed through said openings and a retracted position, gaps between corresponding openings and hollow pistons being less than cross-sectional widths of elastic members stretched around said ends; and
 an actuating rod coupling said trigger and said pistons and configured to cause said pistons to move from said extended position to said retracted position.

2. The device as recited in claim 1 wherein said actuating rod rotates to cause said hollow pistons to move toward said retracted position.

3. The device as recited in claim 1 wherein said actuating rod translates to cause said hollow pistons to move toward said retracted position.

4. The device as recited in claim 1 wherein a surface of said head is configured to seat on an anal dentate of a rectum.

5. The device as recited in claim 1 wherein said openings are evenly spaced in said head.

6. The device as recited in claim 1 further comprising a rectal band ligation button extending laterally from said handle and configured to be depressed to perform ligation with respect to said tissue.

7. The device as recited in claim 1 further comprising a suction indicator associated with said handle and configured to indicate whether or not a suction sufficient for ligation has been drawn.

8. The device as recited in claim 1 further comprising an elastic band deployment indicator associated with said handle and configured to indicate whether or not ligation has been performed.

9. The device as recited in claim 1 wherein said head is of larger diameter than said extension tube.

10. The device as recited in claim 1 wherein said openings lie in a single plane normal to a major axis of said device.

11. A rectal band ligation device, comprising:
 a handle having a trigger associated therewith; an extension tube extending from said handle and terminating in a head, said head being of larger diameter than said extension tube and configured to seat on an anal dentate of a rectum;
 at least two openings in said head;
 hollow pistons located in said openings and configured to move relative thereto between an extended position in which ends of said pistons are exposed through said openings and a retracted position, gaps between corresponding openings and hollow pistons being less than cross-sectional widths of elastic members stretched around said ends; and
 an actuating rod coupling said trigger and said pistons and configured to cause said pistons to move from said extended position to said retracted position.

* * * * *